United States Patent [19]

Bowen

[11] Patent Number: 5,251,646
[45] Date of Patent: Oct. 12, 1993

[54] PROTECTIVE COVERING FOR A SPHYGMOMANOMETER CUFF

[76] Inventor: Thomas Bowen, 13745 SW. 79th Ct., Miami, Fla. 33158

[21] Appl. No.: 905,395

[22] Filed: Jun. 29, 1992

[51] Int. Cl.$^5$ .............................................. A61B 5/00
[52] U.S. Cl. ............................ 128/878; 128/DIG. 15
[58] Field of Search ............... 128/DIG. 15, 677, 917, 128/918, 846, 878

[56] References Cited

U.S. PATENT DOCUMENTS

| | | | |
|---|---|---|---|
| 3,232,289 | 2/1966 | Zimmerman | 128/DIG. 15 X |
| 3,467,077 | 9/1969 | Cohen | 128/DIG. 15 X |
| 3,570,495 | 3/1971 | Wright | 128/DIG. 15 X |
| 3,977,393 | 8/1976 | Kovacic | 128/DIG. 15 X |
| 4,054,952 | 10/1977 | Swallow | 128/DIG. 15 X |
| 4,354,503 | 10/1982 | Golden | 128/677 X |
| 4,711,761 | 12/1987 | Rosenberg | 128/DIG. 15 X |

Primary Examiner—Danton D. DeMille
Assistant Examiner—Sam Rimell
Attorney, Agent, or Firm—Malloy & Malloy

[57] ABSTRACT

A disposable protective covering, structured to completely contain a cuff of sphygmomanometer, the covering including a flexible material sleeve having a front and rear panel which are attached to one another along a top edge and opposite side edges so as to define a pouch wherein the cuff is to be contained. A flap portion formed in the rear panel is adapted to be tucked into the pouch to fully enclose and contain the cuff, the flap portion including an access opening formed there so that hoses attached to the cuff may protrude from the sleeve while the cuff is protectively contained therein, the sleeve being structured for fastening about a user's arm, much like the cuff itself is ordinarily fastened.

7 Claims, 1 Drawing Sheet

PROTECTIVE COVERING FOR A SPHYGMOMANOMETER CUFF

BACKGROUND OF THE INVENTION

1. Field of the Invention

This invention relates to a protective covering adapted to receive and contain completely therein a cuff of a sphygmomanometer while enabling the hoses extending from the cuff to emerge therefrom, thereby providing a safe and effective means of isolating the cuff, which may have been used numerous times and become dirty or contaminated, from the patient upon whom the cuff is placed.

2. Description of the Prior Art

A blood pressure check utilizing a sphygmomanometer is a common and frequently performed medical procedure which in fact is performed routinely on practically all patients. These sphygmomanometers include a cuff which is wrapped around the lower bicep of the user where it is inflated and deflated during the procedure. As a result of the numerous types of equipment connected to the cuff, as well as the cost of the cuff itself, it would be highly expensive to dispose of every cuff after a single or only a few uses. Unfortunately, such a system of disposal would be the ideal circumstance, since often these cuffs may be worn for extended periods of time by a patient, may be used on patients who have been in serious accidents or are otherwise bleeding at or near the area of positioning of the cuff. Additionally, blood is often drawn as a normal procedure, usually at the same time as checking a patient's blood pressure, which along with any cuts or abrasions puts an easily contaminable open wound near the cuff exposing it to possible contamination. Such a desire to sanitize the use of these cuffs is evidenced by the numerous types of disposable cuffs such as those recited in the patents to Weyer, U.S. Pat. No. 3,773,036, and Goldblat, et al., U.S. Pat. No. 3,757,772. Unfortunately, these types of disposable cuffs require complex construction as a result of the numerous hoses which must be attached thereto, are still somewhat expensive for such a frequently performed procedure, and require a complete change of hospital equipment, much of which includes such a cuff integrally formed as part of a complex piece of equipment. For these reasons, it would be highly beneficial to provide a method of sanitizing the use of these cuffs, while not requiring that all existing devices utilizing these cuffs be restructured or eliminated.

In the past, there have been devices such as those recited in Masciarotte, U.S. Pat. No. 4,967,758, and Slaughterbeck, U.S. Pat. No. 4,548,249, which are structured to be used with existing type cuffs. These designs, however, do not provide the complete containment of the cuff as is truly necessary, especially in situations where a patient has suffered an injury which results in bleeding, or is otherwise contagious. More particularly, the disposable cover/liner of Masciarotte is a material layer which is secured to the inside of the cuff, and is thereby susceptible to contact of the exterior portions by the patient, and in more serious situations to the flow of blood should the patient have a wound near the point where the cuff is fastened. The protective sleeve of Slaughterbeck attempts to more completely contain the cuff, however, it includes numerous apertures such that the fastening means of the cuff itself may be exposed, and includes an opening along the top edge which may be readily susceptible to the flow of blood or the like therethrough. The device of the present invention is particularly adapted to completely contain the cuff, allowing only a limited access to the cuff by the hoses which must necessarily be connected thereto. The covering of the present invention can be effectively utilized on existing apparatuses and may be easily interchanged, thereby providing a complete and effective safety measure.

SUMMARY OF THE INVENTION

The present invention is directed towards a protective covering which is adapted to receive and contain therein a cuff of a sphygmomanometer of the type having a plurality of hoses extending therefrom. This covering includes primarily a flexible material sleeve made up of a front panel and a rear panel. This front panel and rear panel, each having a top edge, a bottom edge, and opposite side edges, are attached to one another along the top edge and the opposite side edges so as to define a pouch wherein the cuff may be positioned through an opened lower portion of the pouch. Additionally, the rear panel is generally wider than the front panel so that the lower edge of the rear panel is disposed in spaced apart relation from the lower edge of the front panel, and a flap portion of the rear panel is defined. This flap portion is adapted to be tucked into the pouch through the open lower portion, and thereby completely contains the cuff within the pouch. In order to enable the hoses to protrude from the completely enclosed pouch, an adjustable access opening is formed in the flap portion such that only the limited access necessary to allow passage of the hoses may be provided. The front panel and rear panel which make up the sleeve, each include an outer layer and an inner layer. The inner layer is formed of a flexible, fluid impervious material such that no fluids or contaminants may pass therethrough to contact the cuff or be passed from the cuff to the outside of the protective covering. The outer layer of the front and rear panels is formed of a soft flexible material, thereby making it comfortable to wear and facilitating the fastening thereof. Disposed on an inner layer of the rear panel near the top edge of one of the opposite side edges are fastening means which enable the sleeve to be wrapped and secured about the user's arm in much the same manner that the cuff itself would have been secured. Further, in order to assure that the cuff is securely and stably contained within the pouch, pouch closure means are included along the bottom edge of the front panel so as to contact the flap portion, and stabilizing means are contained within the pouch so as to hold the cuff in place and not allow excessive movement thereof.

It is an object of the present invention to provide a protective covering which will completely contain the cuff of a sphygmomanometer, and will not enable contaminants to pass from the cuff to the outside of the protective covering.

A further object of the present invention is to provide a protective covering which will not enable the cuff to be contaminated or become excessively dirty as a result of the condition of the patient wearing the cuff.

Still another object of the present invention is to provide a protective covering which allows only limited access to the contents thereof, the limited access being adjustable so as to only allow passage of equipment hoses necessarily attached to the cuff.

Another object of the present invention is to provide a protective covering which can be easily removed or positioned, thereby making the often performed and necessary procedure of taking a patient's blood pressure not overly complicated while being completely safe and sanitary.

BRIEF DESCRIPTION OF THE DRAWINGS

For a fuller understanding of the nature of the present invention, reference should be had to the following detailed description taken in combination with the accompanying drawings in which.

Like reference numerals refer to like parts throughout the several views of the drawings.

DETAILED DESCRIPTION OF THE PREFERRED EMBODIMENT

Figure 1:
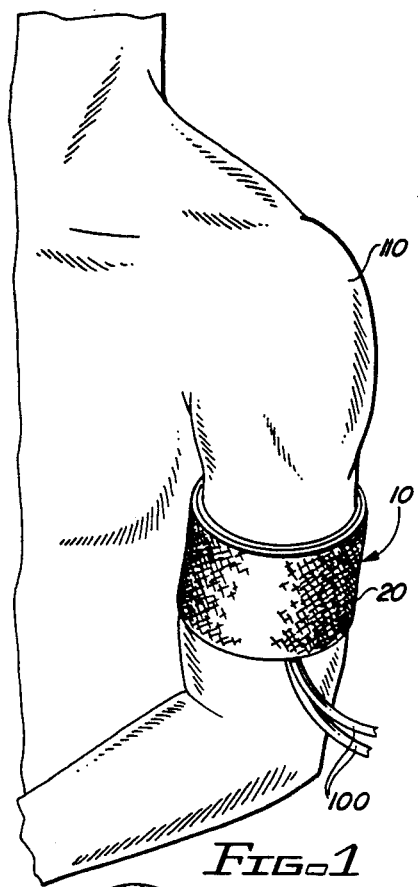
FIG. 1 is a perspective view of the protective covering in use.

As shown throughout FIGS. 1-6, the present invention is directed towards a protective covering, generally indicated as 10, to be used to receive therein and contain a cuff of a sphygmomanometer, of the type having a plurality of hoses 100 extending therefrom. As seen in FIG. 1, the protective covering 10, which primarily includes a flexible material sleeve 20, is adapted to be secured about a user's arm 110 in much the same manner as the cuff itself would have been secured, and does not allow any direct access or contact to the cuff contained with the sleeve 20.

Figure 3:
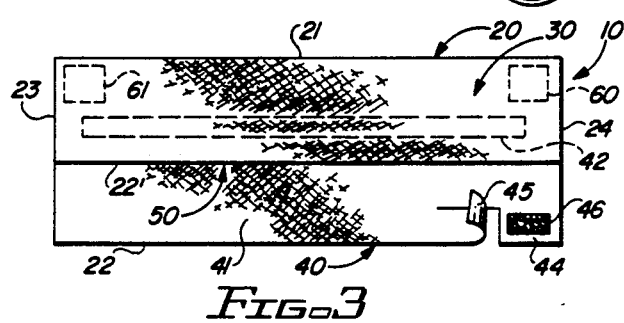
FIG. 3 is a front view of the protective covering.
Figure 4:
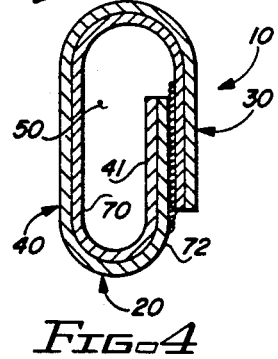
FIG. 4 is a cross-sectional view along line 4—4 of FIG. 2 of the protective covering.

Turning to FIG. 3, the sleeve 20 includes a front panel 30 and a rear panel 40. This front panel 30 and rear panel 40 are attached to one another along their top edges 21 and contacting opposite side edges 23 and 24, so as to define a pouch 50 wherein the cuff is to be received and contained. The rear panel 40 is generally wider than the front panel 30 such that its lower edge 22 is disposed in substantially spaced apart relation from the lower edge 22' of the front panel 30, wherethrough the pouch 50 is accessible, so as to define a flap portion 41. This flap portion 41 is adapted to be tucked into the pouch 50, as best seen in FIG. 4, so as to completely enclose the pouch 50. It should be noted that the opening to the pouch 50 is at the lower edge 22' of the front panel 30 such that any fluids such as blood or the like which naturally flow downward along a patient's arm 110 will not be able to seep in through the opening portion of the sleeve 20. In order to secure the flap portion 41 within the pouch 50, pouch closure means 42 are included within the pouch 50. These pouch closure means 42 are disposed on an inner layer 70 of the front panel 30, and as shown in FIG. 4, both the front panel 30 and rear panel 40 include an inner layer 70 and an outer layer 72. The inner layer 70 is formed of a flexible, fluid impervious material such that no contaminants may pass through the sleeve 20, thereby effectively isolating the cuff contained within the pouch 50. The outer layer 72 is to be formed of a soft, flexible material which will not only be comfortable to wear, but will also be such that, as shown in the preferred embodiment, the pouch securing means 42 may be a hook pad which will effectively engage the outer layer 72 to maintain the pouch 50 sealed, much like if corresponding hook and loop fastener pads were utilized.

Figure 5:
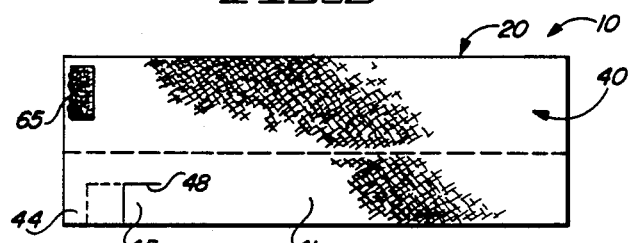
FIG. 5 is a rear view of the protective covering.
Figure 6:
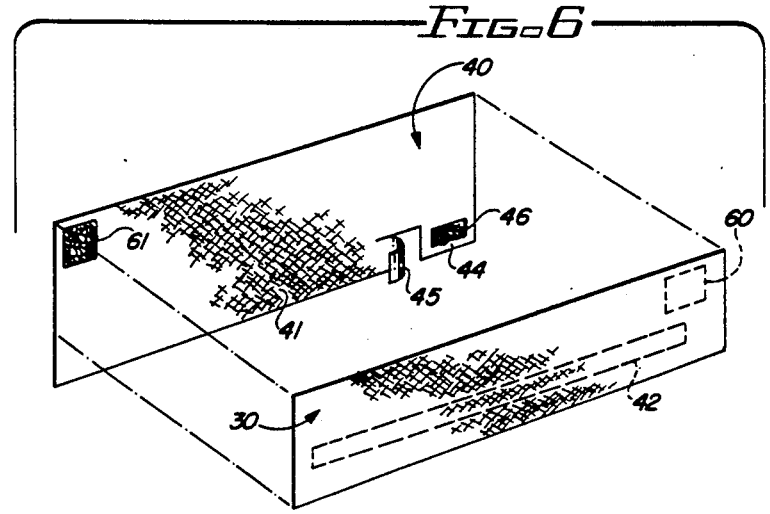
FIG. 6 is an exploded view of the protective covering.

Referring to FIG. 5, fastening means 65 in the form of a hook pad are included on the outer layer 72 of the rear panel 40, such that when the sleeve 20 is wrapped around the arm of a user, the fastening means 65 may be overlapped and contact the outer layer 72 of the front panel 30 in secure attachment about the arm 110 of the user. Additionally, as shown in FIG. 6, stabilizing means 60 and 61 are included within the pouch 50. These stabilizing means are in the form of corresponding hook and loop fastener pads 60 and 61 disposed at opposite ends of the pouch 50 and correspondingly disposed on the front panel 30 and rear panel 40 such that when the cuff is inserted into the pouch 50, the cuff securing means, usually in the form of hook and loop fastener pads, can be correspondingly engaged with the stabilizing means 60 and 61, thereby maintaining the cuff in a secure, non-sliding position within the pouch 50.

Figure 2:
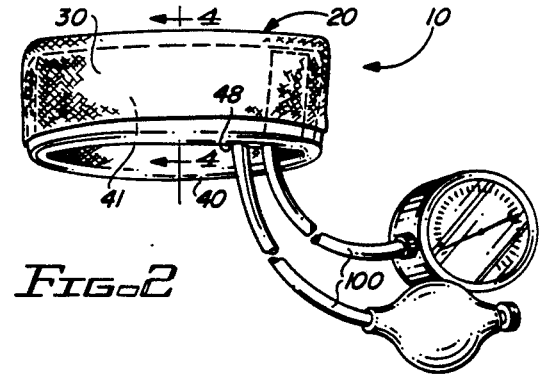
FIG. 2 is a perspective view of the protective covering.

Finally, as best seen in FIGS. 2 and 3, an adjustable access opening 48 is included in the flap portion 41 of the rear panel 40. This access opening 48 is particularly disposed to enable the plurality of hoses 100 which normally extend from the cuff to pass out of the sleeve 20, while not leaving a large opening through which contaminants may flow. This access opening 48 is formed as a result of a pair of perpendicular slits cut into the flap portion 41 which form a vertical strip 44 and a horizontal strip 45. The horizontal strip 45 is adapted to be sufficiently elongate such that it may overlap the vertical strip 44 and engage a hook pad 46 disposed on the inner layer 70 of the vertical strip 44. Accordingly, the hook pad 46 is adjustably adhered to the soft outer layer 72 on the horizontal strip 45 for secure fitting of the access opening 48 about the plurality of hoses 100 which emerge from the sleeve 20.

The protective covering 10, as recited, is the preferred embodiment of the present invention, however, variations consistent with the intent recited by the claims, and in accordance with the doctrine of equivalents, should also be included. Further, the protective covering 10 is structured to be easily adapted to retain cuffs of varying sizes securely therein, as well as allowing these cuffs to freely expand as is necessary during normal use.

Now that the invention has been described, what is claimed is:

1. A protective covering structured and disposed to receive and enclose therein a cuff of a sphygmomanometer, of the type having a plurality of hoses extending therefrom; the protective covering comprising:

a flexible, disposable material sleeve, said sleeve including a front panel and a rear panel, each of said panels including a top edge, a bottom edge, and opposite side edges, said front panel and said rear panel further including an outer layer and an inner layer, said inner layer being formed of a flexible, fluid impervious material, said outer layer being formed of a soft, flexible material.

said front panel being attached to said rear panel along said top edge and said opposite side edges so as to define a punch therebetween, said punch being structured and disposed to receive the cuff therein through an open lower portion thereof, said rear panel being wider than said front panel, such that said lower edge of said rear panel is disposed in substantially spaced apart relation from said lower edge of said front panel, thereby defining a flap portion of said rear panel, said flap portion being structured and disposed to be tucked within said pouch, through said open lower portion of said pouch, so as to substantially surround and enclosure the cuff in protected relation therein, an adjustable access opening formed in said flap portion on said lower edge of said rear panel, said access opening being structured and disposed to allow passage of the hoses attached to the cuff therethrough, said access opening being adjustable in size and including a pair of perpendicularly disposed slits formed in said flap portion so as to form a vertical strip and a horizontal strip, said horizontal strip being sufficiently elongate such that said vertical strip may be disposed in overlying relation thereto, and such that a hook portion on said inner layer of said flap portion on said vertical strip may adhere to said outer layer of said flap portion on said horizontal strip, fastening means disposed on said outer layer of said rear panel at a point near said top edge of one of said side edges of said rear panel, said fastening means being structured and disposed to enable said sleeve to be wrapped about a limb for adjustable, fitted fastening thereabout, pouch closure means disposed along said bottom edge of said front panel on said inner layer, said pouch closure means being structured and disposed to securely close said pouch so as to completely contain the cuff therein, and stabilizing means disposed within said pouch, said stabilizing means being structured and disposed to hold the cuff non-slidably within said pouch.

2. A protective covering as in claim 1 wherein said fastening means includes a hook pad structured and disposed to removably adhere to said soft, flexible material outer layer of said front panel, such that said sleeve may be securely wrapped about the user's arm.

3. A protective covering as in claim 2 wherein said pouch closure means includes a hook pad structured and disposed to removably adhere to said soft, flexible material outer layer of said rear panel, such that said flap portion may be adjustably positioned to contain said cuff within said pouch.

4. A protective covering as in claim 3 wherein said stabilizing means includes a hook and a loop fastener pad disposed within said pouch, at opposite distal ends of said pouch, so as to removably adhere to corresponding hook and loop fastener pads on the cuff.

5. A protective covering as in claim 4 wherein said sleeve is sized to contain cuffs to varying sizes, and enable said cuff to expand during use.

6. A protective covering as in claim 5 wherein said outer layer and said inner layer are made of a durable, washable material.

7. A protective covering structured and disposed to receive and enclosure therein a cuff of a sphygmomanometer, of the type having a plurality of hoses extending therefrom; the protective covering comprising:

a flexible, disposable material sleeve, said sleeve including a front panel and a rear panel, each of said panels including a top edge, a bottom edge, and opposite side edges, said front panel and said rear panel further including an outer layer and an inner layer, said inner layer being formed of a flexible, fluid impervious material, said outer layer being formed of a soft, flexible material, said front panel being attached to said rear panel along said top edge and said opposite side edges so as to define a pouch therebetween, said pouch being structured and disposed to receive the cuff therein through an open lower portion thereof, said rear panel being wider than said front panel, such that said lower edge of said rear panel is disposed in substantially spaced apart relation from said lower edge of said front panel, thereby defining a flap portion of said rear panel, said flap portion being structured and disposed to be tucked within said pouch, through said open lower portion of said pouch, so as to substantially surround and enclose the cuff in protected relation therein, an adjustable access opening formed in said flap portion on said lower edge of said rear panel, said access opening being structured and disposed to allow passage of the hoses attached to the cuff therethrough, said access opening being adjustable in size and including a pair of perpendicularly disposed slits formed in said flap portion so as to form a vertical strip and a horizontal strip, said horizontal strip being sufficiently elongate such that said vertical strip may be disposed in overlying relation thereto, and such that a hook portion on said inner layer of said flap portion on said vertical strip may adhere to said outer layer of said flap portion on said horizontal strip, fastening means disposed on said outer layer of said rear panel at a point near said top edge of one of said side edges of said rear panel, said fastening means being structured and disposed to enable said sleeve to be wrapped about a limb for adjustable, fitted fastening thereabout, pouch closure means disposed along said bottom edge of said front panel on said inner layer, said pouch closure means being structured and disposed to securely close said pouch so as to completely contain the cuff therein, and stabilizing means disposed within said pouch, said stabilizing means being structured and disposed to hold the cuff non-slidably within said pouch and including a hook and loop fastener pad disposed within said pouch at opposite distal ends of said pouch, and being positioned and disposed to adhere to corresponding hook and loop fastener pads on the cuff.

* * * * *